US005478754A

United States Patent [19]
Brandt et al.

[11] Patent Number: 5,478,754
[45] Date of Patent: Dec. 26, 1995

[54] DETERMINATION OF GLYCATED HEMOGLOBIN BY FLUORESCENCE QUENCHING

[75] Inventors: Douglas R. Brandt, Mundelein; William E. Brown, Libertyville; Theresa L. Lane, Evanston, all of Ill.

[73] Assignee: Abbot Laboratories, Abbott Park, Ill.

[21] Appl. No.: 167,729

[22] Filed: Dec. 15, 1993

Related U.S. Application Data

[62] Division of Ser. No. 845,908, Mar. 4, 1992, abandoned.

[51] Int. Cl.$^6$ .................................................... G01N 33/72
[52] U.S. Cl. ........................ 436/518; 435/7.1; 435/968; 435/14; 436/538; 436/539; 436/66; 436/67
[58] Field of Search .............................. 422/70; 435/7.1, 435/803, 968.14; 436/501, 518, 538, 66, 67, 523, 539; 536/17.1, 21

[56] References Cited

U.S. PATENT DOCUMENTS

| | | | |
|---|---|---|---|
| 4,168,147 | 9/1979 | Acuff | 436/67 |
| 4,238,196 | 12/1980 | Acuff et al. | 436/67 |
| 4,243,534 | 1/1981 | Bulbenko | 436/67 |
| 4,255,385 | 3/1981 | Stroupe et al. | 436/67 |
| 4,269,605 | 5/1981 | Dean et al. | 432/61 |
| 4,407,961 | 10/1983 | Sanders | 436/67 |
| 4,438,204 | 3/1984 | Deeg et al. | 436/67 |
| 4,621,049 | 11/1986 | Wang | 435/805 |
| 4,649,122 | 3/1987 | Lee | 436/67 |
| 4,861,728 | 8/1989 | Wagner et al. | 436/501 |
| 5,110,745 | 5/1992 | Kricka et al. | 436/67 |
| 5,116,763 | 5/1992 | Greene et al. | 435/14 |

FOREIGN PATENT DOCUMENTS 2181840  4/1987  United Kingdom.

OTHER PUBLICATIONS

K. Horiuchi et al, "A Reaction Cell for Simultaneous Measurements of Fluorescence and Absorption in a Hemoglobin Solution . . . ", Biochem. Biophys. Res. Commun. vol. 97 No. 2 (1980) pp. 811–818.
T. Kuwajima et al, "Synthesis of Fluorescent Organic Phosphates and Their Equilibruim Binding to Bovine Oxyhemoglobin", Biochemistry vol. 14 No. 3 (1975) pp. 492–497.
R. Little et al, "Interlaboratory Standardization of Measurements of Glycohemoglobins", Clin. Chem. vol. 38 No. 12 (1992) pp. 2472–2478.
D. Wilson et al, "Fully Automated Assay for Glycohemoglobin . . . " Clin. Chem. vol. 39 No. 10 (1993) pp. 2090–2097.
C. Pennington et al, "An Automated Digoxin Assay on the IM® System Using Soluble Reagents and Polyelectrolyte Interaction as Separation Means", Clin. Chem. vol. 37, No. 6 (1991) p. 1046 Abstract No. 0650.
Huisman et al; Clin. Chim. Acta 5:103–123 (1960).
Janado et al; Agr. Biol. Chem. 37(10):2337–443 (1973).
Abraham et al; Diabetes 27(9):931–937 (1978).
Pecoraro et al; Diabetes 28:1120–1125 (1979).
Gould et al; Clin. Chem. 28(10):2088–2094 (1982).
Klenk et al; Clin. Chem. 28(10):2088–2094 (1982).
Yue et al; Diabetes 31:701–705 (1982).
Abraham et al; J. Lab. Clin. Med. 102:187–197 (1983).
Garlick et al; J. Clin. Invest. 71:1062–1072 (1983).
Middle et al; Biochem. J. 209:771–779 (1983).
Talwar et al; Clin. Chim. Acta 128:61–67 (1983).
Maria Bryszewska, Department of Biophysics, University of Lodz, Lodz, Poland Interaction of Normal and Glycated Human Haemoglobin with Erythrocyte Membranes from Normal and Diabetic Individuals, Sep. 8, 1988, J. Clin. Chem. Clin. Biochem., vol. 26, 1988, pp. 809–813.

*Primary Examiner*—Carol A. Spiegel

[57] ABSTRACT

The present invention relates to the measurement of glycated hemoglobin by fluorescence quenching. The present invention uniquely involves performing two sequential fluorescent quenching measurements: one measurement of the fluorescent quenching due to total hemoglobin in the sample and a second measurement of the fluorescent quenching due to glycated hemoglobin present in the sample after the non-glycated hemoglobin is removed. Glycated hemoglobin and non-glycated hemoglobin can be separated by a variety of methods as described herein, including ion capture and phase separations.

22 Claims, 3 Drawing Sheets

DETERMINATION OF GLYCATED HEMOGLOBIN BY FLUORESCENCE QUENCHING

This application is a Division of application Ser. No. 07/845,908, filed Mar. 4, 1992, now abandoned.

BACKGROUND OF THE INVENTION

Glycated hemoglobin is a generic term referring to a series of minor hemoglobin components that are formed via the attachment of various sugars, most commonly glucose, to the hemoglobin molecule. The most important of these minor hemoglobin components in respect to diabetes is hemoglobin $A_{1c}$. It is formed by the attachment of glucose to the N-terminal amino acid residue, valine, on one or both β chains of hemoglobin A (Goldstein, D. E., et al., Clin. Chem. 32:B64-B70, 1986).

The human erythrocyte is freely permeable to glucose. Within each erythrocyte, glycated hemoglobin is formed from hemoglobin A (the native, normal form) at a rate proportional to the ambient glucose concentration. The reaction is spontaneous, not enzyme catalyzed, but slow enough that only a fraction of the hemoglobin is modified during the life span of the erythrocyte (120 days) and is irreversible. As a result, glycated hemoglobin provides a weighted "moving" average measure of past blood glucose levels with more recent glucose levels having a greater influence (Singer, et al., Ann. Clin. Biochem. 26:213–219, 1989).

Elevated levels of glycated hemoglobin are known to be associated with diabetes mellitus. Glycated hemoglobin is present in non-diabetics at a level of about 5% of total hemoglobin, while diabetics have 2–4 times that amount. Glycated hemoglobin levels are relatively unaffected by short-term (hour-to-hour) fluctuations in blood sugar level and, hence give a relatively precise reflection of the state of blood glucose control in diabetics. The results are indicative of the time-average blood glucose concentration over the past 1 to 3 months. Glycated hemoglobin measurements are used in the assessment of the severity of glucose intolerance in a diabetic patient and in management of diabetes mellitus (Lester, Ann. Clin. Biochem. 26:213–219, 1989; Kennedy, et al., Br. Med. Bull. 45:174–190, 1989; Fluckiger, et al., J. Chromatogr. 429:279–292, 1988: Goldstein, et al., Clin. Chem. 32:B64–70, 1986; Mortensen, Dan. Med. Bull. 32:309–328, 1985; Goldstein, et al., CRC Crit. Rev. Clin. Lab. Sci. 21:187–228, 1984; Peacock, J. Clin. Pathol. 37:841–851, 1984; Miedema, et al., Ann. Clin. Biochem. 21:2–15, 1984; Mayer, et al., Clin. Chem. Acta 127:147–184, 1983; Gabbay, Med. Clin. North Am. 66:1309–1315, 1982).

There are various methods for measuring glycated hemoglobin; as hemoglobin $A_{1c}$ or hemoglobin A1, or as total glycated hemoglobin (ion-exchange chromatography, thiobarbituric acid method, isoelectric focusing, and affinity chromatography assays) (Cole, R. A., et al., Metabolism 27:289–301, 1978; Nathan, D. M., Clin. Chem. 27:1261–1263, 1981; Moore, J. C., et al., Ann. Clin. Biochem. 23:85–91, 1986). In ion-exchange chromatography many glycated hemoglobin species, including hemoglobin $A_{1c}$, are less positively charged at neutral pH than hemoglobin $A_o$, and bind less well to a negatively charged resin (Rosenthal, P. K., et al., AM. J. Clin. Pathol. 75:45–49, 1981; U.S. Pat. Nos. 4,407,961, 4,649,122). A few methods have been described that separate hemoglobin $A_{1c}$ from hemoglobin $A_{1a+b}$ fraction (Goldstein, D. E., et al., Diabetes 31:70–78, 1982; Maquart, F. X., et al., Clin. Chim. Acta 108:329–332, 1980; Jones, M. D., et al., Hemoglobin 2:53–58; 1978; Clarke, J. T., et al., Diabete Metabol. 5:293–296, 1979; Davis, J. E., et al., Diabetes 27:102–107, 1978; Cole, R. A., et al., Metabolism 27:289–301, 1978; U.S. Pat. No. 4,389,491; Bio-Rad Laboratories, Hemoglobin $A_{1c}$ Micro Column Test Instruction Manual, March 1990). However, these methods suffer from one or more disadvantages. Many of the methods involve the use of two buffers, the first to elute nonbound material from the ionexchange resin in such a way that does not cause the desorption of the specifically bound material. A second buffer, used at a different pH, ionic strength or containing a competitive inhibitor is needed to elute the specifically bound material. The temperature, pH, ionic strength or the presence of a competitive inhibitor is needed to elute the specifically bound material. The temperature, pH, ionic strength, and column size affect the test results (Simon, M., et al., Diabetes 29:467–474, 1980; Schellekens, A. P. M., et al., Clin. Chem. 27:94–99, 1981; Castagnola, M., et al., J. Chromatogr. 272:51–65, 1983). Moreover, the methods require several different steps, several vessels, and most of the methods are nonautomated or only semiautomated.

Other limitations to these assays, depending on the method used, include a reversible intermediate glycated form, "pre-hemoglobin-Alc", which needs to be removed before the assay is done (Goldstein, D. E., et al., Diabetes 31:70–78, 1982; Bunn, H. F., Diabetes 30:613–617, 1981; Nathan, D. M., Clin. Chem. 27:1261–1263, 1981; Mayer, T. K., et al., Clin. Chim. Acta 127:147–184, 1983; Health and Public Policy Committee, American College of Physicians Ann. Intern Med. 101:710–713, 1984) (Nathan, D. M. Clin. Chem. 27:1261–1263, 1981). High levels of fetal hemoglobin, sickle hemoglobin, and other rarer conditions may interfere with the assay (Niejadlik, D. C., et al., JAMA 224:1734–1736, 1973).

Other methods of determining glycated hemoglobin use specific affinity or binding agents to bind glycated hemoglobin. In the following patents, U.S. Pat. Nos. 4,200,435; 4,260,516; 4,274,978; 4,255,385, and 4,438,204, glycated hemoglobin is determined using affinity methods or the allosteric properties of hemoglobin. In DE Patent 1595 69, a sugar-binding protein as an affinity reagent is described.

Other affinity binding methods are based on specific complex formation between glycated hemoglobin and boronic acid derivatives (Middle, et al., Biochem. J. 209:771–779, 1983; Klenk, et al., Clin. Chem. 28:2088–2094, 1982; Little, et al., Clin. Chem. 32:358–360, 1986, U.S. Pat. Nos. 4,269,605; 4,861,728; UK Patent Application GB 2 206 411 A; Isolab, Inc. Technical Publication:Glyc-Affin™ GHb, 1986; Forrest, R. D., et al., Clin. Chem. 34:145–148, 1988). Although affinity binding methods detect glycated hemoglobin species in addition to $HbA_{1c}$, they correlate linearly with methods more specific for $HbA_{1c}$, such as ion-exchange chromatography (Little, et al., Clin. Chem. 32:358–360, 1986). Like the ion-exchange and colorimetric assay for glycated hemoglobin, the affinity methods also have limitations. One of the limitations is that two different buffers are required. The first buffer elutes the non-glycated fraction, which does not have cis-diol groups. The bound fraction, rich in glycated hemoglobin is eluted with a second buffer which contains a displacing agent, such as a sugar alcohol, that displaces glycated hemoglobin from the column. Additionally, the flow rate and size of the column limits the amount of hemoglobin bound to the affinity agent.

There is a need for a glycated hemoglobin assay that is easy to perform, free from interferences and relatively insensitive to experimental variables such as pH and temperature. An object of the present invention is to develop an assay method and reagents to perform glycated hemoglobin measurements accurately and with precision.

SUMMARY OF THE INVENTION

The present invention relates to the measurement of glycated hemoglobin by fluorescence quenching. Although glycated hemoglobin and normal hemoglobin both quench fluorescence to the same degree, the inventors unexpectedly discovered that fluorescence quenching may be used to estimate the glycated hemoglobin levels in blood samples. The present invention uniquely involves performing two sequential fluorescent quenching measurements: one measurement of the fluorescent quenching due to total hemoglobin in the sample and one measurement of the fluorescent quenching due to glycated or non-glycated hemoglobin present in the sample. Glycated hemoglobin and nonglycated hemoglobin can be separated by a variety of methods as described herein, including ion capture and solid phase separations.

DETAILED DESCRIPTION OF THE INVENTION

Figure 1:
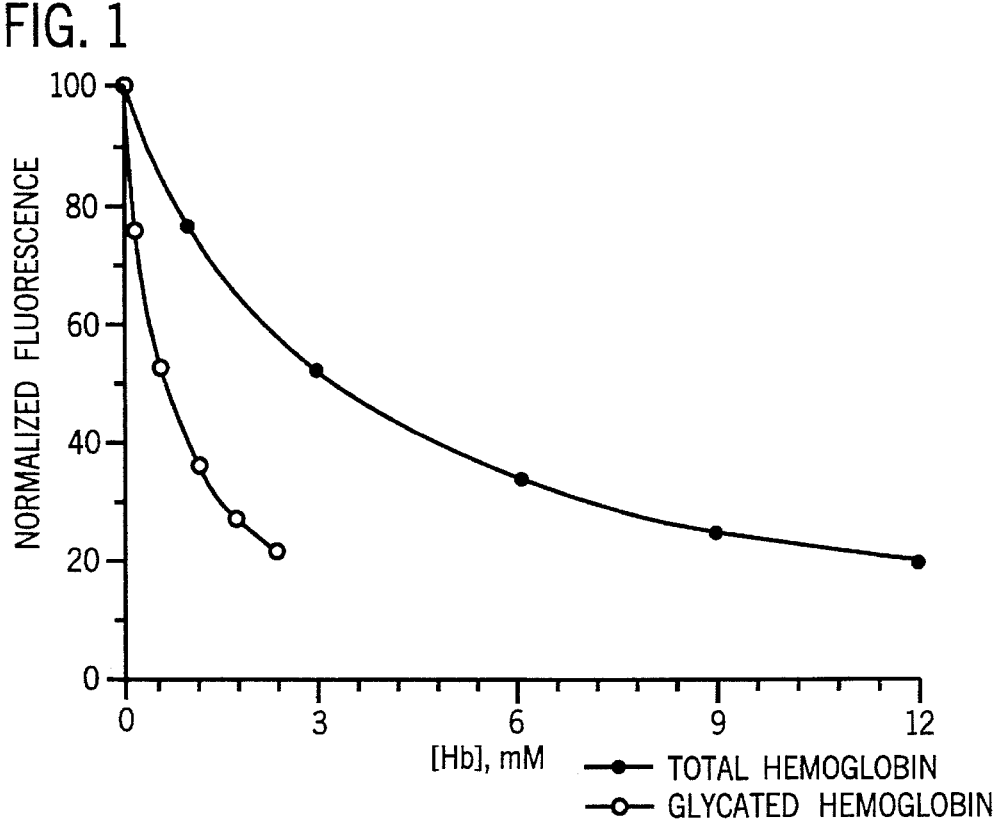
FIG. 1: Typical calibration curves (% Fluorescence relative to the A calibrator versus hemoglobin concentration in mM) for total hemoglobin and glycated hemoglobin using the calibrators listed in Table 1 in the assay format of Example 6 of the present invention.

The present invention relates to the measurement of glycated hemoglobin by fluorescence quenching. Although glycated hemoglobin and normal hemoglobin both quench fluorescence to the same degree, the inventors unexpectedly discovered that fluorescence quenching may be used to estimate the glycated hemoglobin levels in blood samples. The present invention uniquely involves performing two sequential fluorescent quenching measurements: one measurement of the fluorescent quenching due to total hemoglobin in the sample and a second measurement of the fluorescent quenching due to glycated hemoglobin present in the sample after the non-glycated hemoglobin is removed. Glycated hemoglobin and non-glycated hemoglobin can be separated by a variety of methods as described herein, including ion capture and solid phase separations.

Fluorescence quenching involves the ability of certain molecules, such as the heme moiety of hemoglobin, to absorb the excitation energy of neighboring fluorescent compounds which have been exposed to incident excitation radiation. Normally, a fluorescent compound exposed to incident excitation radiation at the proper wavelength absorbs energy (excitation) and then releases the energy in the form of fluorescence radiation. When in the excited state, the fluorescent compound can also release the absorbed energy by transferring the energy to another agent, such as a quencher compound like the heme of hemoglobin. This energy transfer reduces the amount of fluorescence that normally would be produced and is referred to as quenching.

As a first step in the determination of glycated hemoglobin in blood samples it is necessary to lyse the red blood cells. Lysing of the blood cells releases both glycated hemoglobin and non-glycated hemoglobin from the cells. Common cationic (e.g., cetyl trimethyl ammonium bromide), anionic (e.g., sodium dodecylsulfate and sodium deoxycholate) and neutral (e.g., saponin and polyoxyethylene) detergents are useful in lysing red blood cells. Neutral detergents, like saponin, in the concentration range of about 0.1 to 5% (v/v) are preferred and more preferably concentrations within the range of about 0.5% to about 2% (v/v). Mechanical rupture, for example, ultrasonication and hypotonic lysis, are also effective ways of releasing hemoglobin from red blood cells. Preferably, red cell lysis is accomplished adding a detergent, such as TRITON, an alkyl substituted polyoxythelene X-100 at approximately 0.5%, followed by two cycles of rapidly aspirating and dispensing the mixture into and out of a pipet. This process gave almost instantaneous hemolysis of fresh whole blood.

In a preferred method, after lysing the red blood cells, the sample is contacted with an indicator reagent having a detectable fluorescent signal. A first measurement of the fluorescent quenching caused by the mixture of glycated hemoglobin and non-glycated hemoglobin (total hemoglobin) is obtained. The glycated hemoglobin and the non-glycated hemoglobin are separated and a second measurement of the fluorescent quenching caused by the glycated or non-glycated hemoglobin is obtained. The percent glycated hemoglobin can then be calculated from these two measurements.

In an alternative preferred method, after lysing the red blood cells, the sample is contacted with an indicator reagent having a detectable fluorescent signal and the glycated hemoglobin and the non-glycated hemoglobin are separated. A first measurement of the fluorescent quenching caused by the glycated or non-glycated hemoglobin is obtained. Then a second measurement of the fluorescent quenching caused by both the glycated hemoglobin and the non-glycated hemoglobin is obtained. This second measurement can be accomplished by either measuring the fluorescence quenching due to total hemoglobin or by measuring fluorescence quenching due to the nonglycated hemoglobin and adding this value to the first measurement. The percent glycated hemoglobin can then be calculated from the first and second measurements.

In yet another preferred method, the indicator reagent is incorporated, directly or indirectly, onto a solid phase or matrix used in the separation of glycated hemoglobin and non-glycated hemoglobin.

An indicator reagent comprises a fluorescent compound whose fluorescence is measurably quenched by hemoglobin. Fluorescent compounds which may be used in this invention include methylumbelliferone and other coumarins, fluorescein, rhodamine, and the like.

The separation of glycated hemoglobin and the non-glycated hemoglobin can be performed by a variety of methods. In a preferred embodiment, a specific binding member specific for glycated hemoglobin is used in the separation process. A specific binding member as used herein means a member of a specific binding pair, i.e., two different molecules where one of the molecules through chemical or physical means specifically binds to the second molecule. Specific binding member includes dihydroxyboryl moieties, lectins, monoclonal or polyclonal antibodies, such as anti-HbA1c antibodies, and other binding proteins including recombinant proteins. An exemplary monoclonal anti-HbA1c antibody is described in Knowles, et al., U.S. Pat. No. 4,727,036. Lectins that have specificity for alpha-D-glucose include Concanavalin A, Succinyl-Con A, and *Vicia fava* and the like. Other lectins and their carbohydrate specificities are well known and available as free lectin bound to a solid support, e.g. Sepharose™-lectin. Other carbohydrate specific supports include alumina gel, calcium phosphate gel, magnesium carbonate, magnesium silicate and silica gel.

A preferred specific binding member specific for glycated hemoglobin is the dihydroxyboryl moiety as described in U.S. Pat. No. 4,269,605, which is incorporated herein by reference. The moiety is preferably phenyl or substituted phenyl boronic acid, boric acid or other boronic acids, such as ethaneboronic acid and 1-propaneboronic acid, and the like. The boronate must first be in the tetrahedral anionic form before this reaction can effectively occur (ie., the pH of the solution must be greater than the pK of the boronate). Through a mechanism that is not well understood, tetrahedral boronate can exchange hydroxyls with a 1,2-cis-diol, releasing two water molecules and forming the five-membered ring covalent complex.

Preferably, the boronate/diol complexes are formed in the presence of buffers that serve to strengthen the boronate/diol complex. Buffers compatible in this test system are buffers having a pKa in the approximate range of 7.5 to 11.0. Buffers within this range are known in the art. More preferred are buffers with pKa's of approximately 8.5 to 9.2, in order to maintain the pH during the assay in the pH range of approximately 7.8 to 9.6 at 37° C., more preferably between approximately 8.5 to 9.2, most preferably in the range of 9 to 9.2. Amines may serve to strengthen the complex, thus buffers such as glycine, morpholine, HEPES, or additives such as ammonium salts or piperadine may be advantageous to promote boronate/diol complex formation. Unprotonated amines can serve as electron donors to form a neutral complex with boronate in which there is negative charge density on the boronate, and positive charge on the amine. In this state, two boron hydroxyls are still available for binding to 1,2-cis-diols such as glycated hemoglobin. Preferably, an amino buffer, such as HEPES buffer, is added to the boron/diol reaction, preferably, in the red cell lysis reaction. Amines appear to strengthen the boronate/diol complexes formed, possibly by lowering the apparent pKa of the boronate. However, hydroxyl-amino buffers, such as Tris buffer, can interfere with the boronate/diol complex formation by complexing with the boron.

Preferably, the boronate/diol complex is formed in the presence of $Mg^{2+}$. U.S. patent application Ser. No. 717,558, entitled "Rapid Determination Of Glycated Hemoglobin", which enjoys common ownership and is herein incorporated by reference, Middle, et al. Biochem. J. 209:771–779 (1983), and in Boronate Ligands in Biochemical Separations, Publication 501, Amicon Corporation (1981) describe the use of divalent cations, primarily $Mg^{2+}$ derived from $MgCl_2$ or $MgSO_4$, to overcome the repulsion between the negatively charged boronate and negatively charged ligands. The present invention also uses $Mg^{+2}$ for this purpose. However, the present invention preferably uses $MgSO_4$ instead of $MgCl_2$, which allows the invention to operate optimally. The preferred concentration og $MgSO_4$ is approximately 10– 500 mM, more preferably 50–200 mM, and most preferably about 100 to 150 mM.

Preferably, the separation process is accomplished by contacting the sample of lysed blood cells containing glycated and non-glycated hemoglobins with a solid phase having bound thereto a specific binding member specific for glycated hemoglobin and separating the solid phase and the remainder of the sample. The specific binding member may be bound to the solid phase by physical or chemical means, preferably by means of a direct covalent bond. The specific binding member should be bound to the solid phase in such a way that substantially all of the specific binding member does not detach during subsequent reactions. Regardless of the specific binding member and the coupling method selected, the specific binding member must be able to bind to the glycated hemoglobin. For example, regardless of the dihydroxyboryl moiety and the coupling method selected, the dihydroxyboryl moiety must be able to bind to the sugar moiety of the glycated hemoglobin.

A solid phase according to the present invention may be a mixture of polymeric microparticles with chemically or physically bound specific binding members specific for glycated hemoglobin. Microparticles that can be used include polystyrene, carboxylated polystyrene, polymethylacrylate or similar particles with a radius ranging from about 0.1 μm to about 0.25 inches. A preferred separation method for these particles is the use of microparticle capture on a porous matrix such as glass fiber.

Other solid phases that can be used include a mixture of magnetizable polymeric microparticles with chemically or physically bound specific binding members specific for glycated hemoglobin. Magnetizable microparticles that can be used preferably have ferric oxide or chromium oxide cores and a polystyrene, carboxylated polystyrene or polymethylacrylate coating. Yet other solid supports are known to those in the art and include the walls of wells of a reaction tray, test tubes, polystyrene beads, nitrocellulose strips, membranes and the like. Natural, synthetic, or naturally occurring materials that are synthetically modified, can be used as a solid phase material including polysaccharides, e.g., cellulose materials such as paper and cellulose derivatives such as cellulose acetate and nitrocellulose; silica; inorganic materials such as deactivated alumina, diatomaceous earth, $MgSO_4$, or other inorganic finely divided material uniformly dispersed in a porous polymer matrix, with polymers such as vinyl chloride, vinyl chloride-propylene copolymer, and vinyl chloride-vinyl acetate copolymer; cloth, both naturally occurring (e.g., cotton) and synthetic (e.g., nylon); porous gels such as silica gel, agarose, dextran, and gelatin; polymeric films such as polyacrylamide; and the like. The solid phase material should have reasonable strength or strength can be provided by means of a support, and it should not interfere with the production of a detectable signal.

An alternative preferred separation method is the method described in co-pending U.S. patent application Ser. No. 150,278 and U.S. patent application Ser. No. 375,029, both of which enjoy common ownership and both of which are incorporated herein by reference. These applications describe the use of ion capture separation, in which the specific binding members used in the assay in question are chemically attached to a first polyionic compound and a porous matrix having bound thereto a second polyionic compound that binds to the first polyionic compound. A specific binding pair is formed and separated from the reaction mixture by an electrostatic interaction between the first and second polyionic compounds. The specific binding member is preferably covalently coupled to the first polyionic compound.

Preferably, the first polyionic compound is a polyanionic acid, such as polyaspartic acid, heparin, carboxymethyl amylose, polyglutamic acid or polyacrylic acid, and the second polyionic compound is a cationic polymer, such as GafQuattm which is a polymeric quaternary ammonium compound (GAF Corporation, Wayne, N.J., 07470), diethylaminoethyl-dextran (Sigma Chemical Company, St. Louis, Mo.),-water soluble cellulose derivatives such as Celquat™ L-200 and Celquat™ H-100 (National Starch & Chemical Corporation, Bridgewater, N.J., 08807) which are both polymeric quaternary compounds, or Merquat® 100 a cationic homopolymer of dimethydiallyammonium chloride (commercially available from Calgon Corporation). The porous matrix is treated with the cationic polymer to render the matrix positively charged. The cationic polymer is bound to the matrix by absorption, adsorption, or covalent or ionic coupling. The separation of the reaction products is effected by the electrostatic interaction between the positively charged pad and the negatively charged polyanion complex.

The porous matrix can include any suitable porous material. By "porous" is meant that the material is one through which fluids can flow and can easily pass. In the present invention, the matrix can include a polypropylene, polyethylene, Teflon, fiberglass, cellulose, or nylon pad or other porous material well known to those skilled in the art for use in a pour and flow-through assay device having one or more layers containing one or more of the assay reagents.

Preferred solid phase materials include a porous fiberglass material, such as a "Whatman 934-AH" filter paper, which has a nominal thickness of 0.33 mm, or the disposable IMx® cartridge and TestPack™ (fiber matrix) devices of Abbott Laboratories (Abbott Park, Ill., 60064). The thickness of such material is not critical, and will be a matter of choice, largely based upon the properties of the sample or analyte being assayed, such as the fluidity of the test sample.

The actual fluorescence quenching by hemoglobin can be measured by any method known to the art. For example, a fluorescence spectrometer is desirable, although the fluorescence spectrum can be observed with a visual spectrometer or photographed with a spectrograph of high light-gathering power. In a preferred embodiment, the fluorescence is detected using an IMx® (Abbott Laboratories, Inc.) automated benchtop analyzer that contains an optical assembly which is a fluorometer that uses a mercury arc lamp as its light source. This instrument is described by Fiore, M. et al 1988. Clin. Chem 34/9:1726–1732, the contents of which are incorporated herein by reference. The fluorescence quenching observed is proportional to the hemoglobin present in the sample being measured.

In a most preferred method, two fluorescence measurements are taken sequentially using the same fiber matrix, such as the IMx® disposable cartridge (commercially available from Abbott Laboratories, Ill.). The red blood cells in the sample are lysed. The hemolysate is diluted in a first container or well by mixing an aliquot of the hemolysate with an aqueous buffer, such as HEPES buffer, and the hemolysate is diluted in a second container or well by mixing an aliquot of the hemolysate with an aqueous buffer, such as HEPES buffer, containing a specific binding member specific for glycated hemoglobin bound to either a microparticle or a polyionic compound, such as meta-aminobenzeneboronic acid covalently coupled to a latex microparticle or to polyacrylic acid (alternatively, the borate particles or polymer can be added to the lysis solution). Boronate glycated hemoglobin complexes are formed in the mixture in the second container, but not in the first container. An aliquot of the mixture in the second container is transferred to a fiber matrix, such as glass fiber or glass fiber coated with a polyionic compound, such as Merquat, that binds to the first polyionic compound. Boronate glycated hemoglobin complexes are captured by the matrix and the matrix is washed with a wash buffer which also contains a fluorescent compound, such as 4-methylumbelliferone (alteratively and preferably, the fluorescent compound can be present in every solution used in the assay). The wash removes non-glycated hemoglobin and the fluorescence of the matrix is measured. The fluorescence quenching measured is due to the glycated hemoglobin present on the matrix. The matrix is then washed with a solution containing a cis-1,2-diol compound, such as a sugar like sorbitol. The cis-1,2-diol compound is preferably also added to the mixture in the first container. Sorbitol competes with glycated hemoglobin for the bound affinity reagent and the glycated hemoglobin is removed. Preferably, a wash solution containing a sorbitol concentration within the range of about 1 to about 30% (w/v), more preferably, at a concentration within the range of about 5 to about 30% and most preferably, at a concentration of 10%. Other compounds that disrupt the boronate glycated hemoglobin complexes can also be used, such as 1,2-aminohydroxy compounds like Tris buffer. An aliquot of the mixture in the first container is transferred to the washed matrix and the fluorescence of the matrix is measured. The fluorescence quenching measured is due to both glycated and non-glycated hemoglobin. The total and glycated hemoglobin concentrations can then be determined from their respective calibration curves and the % of glycated hemoglobin in total hemoglobin is calculated.

Calibration curves are generally prepared from calibrator solutions containing known glycated hemoglobin or hemoglobin concentration. U.S. patent application Ser. No. 717, 558, entitled "Rapid Determination Of Glycated Hemoglobin", which enjoys common ownership and is herein incorporated by reference, discloses stable glycated hemoglobin calibrators and controls that are useful in glycated hemoglobin assays. Preferably six calibrators are used to obtain a calibration curve, though more or less calibrators can be used depending on the accuracy and precision of the result desired. Preferably, the calibrators contain increasing amounts of hemoglobin ([Total Hb]) and glycated hemoglobin ([Gly Hb]), but the ratio of glycated hemoglobin to total hemoglobin (% Gly Hb) can be held constant. For example, Table 1 illustrates the composition of one set of calibrators (see Example 4). One skilled in the art would be capable of devising other calibrator and control formulations. Controls are generally used in conjunction with an assay to confirm the viability of a calibration curve or assay reagents. Preferably, the formulation of the controls are the same as the calibrators with the exception that the percent glycated hemoglobin, the hemoglobin concentration and glycated hemoglobin concentration may not be identical with any one of the calibrators.

TABLE 1

| Calibrator | [Total Hb] | [Gly Hb] | % Gly Hb |
|---|---|---|---|
| F | 12 | 2.4 | 20 |
| E | 9 | 1.8 | 20 |
| D | 6 | 1.2 | 20 |
| C | 3 | 0.6 | 20 |
| B | 1 | 0.2 | 20 |
| A | 0 | 0.0 | 0 |

To maintain aseptic conditions throughout the procedure, it may be desirable to add a small quantity of an antimicrobial agent to the system which may include solvents, antibiotics and poisons. Other biochemicals, e.g., KCN in the determination of glycated hemoglobins, may be introduced to the lysed blood sample.

The following examples are illustrative of the invention and are in no way to be interpreted as limiting the scope of the invention, as defined in the claims. It will be appreciated that one skilled in the art can conceive of many other devices and methods of use to which the present inventive concepts can be applied.

EXAMPLE 1

Fifty microliters (50 μL) of a hemoglobin sample (see Table 2) were mixed with 200 μL of 0.25 mM methylumbelliferone in 50 mM ammonium acetate buffer at pH 8.0 containing 50 mM $MgCl_2$ and 50% (v/v) dihydroxyboryl resin (Glyco-gel, commercially available from Pierce Chemical Company, Ill.). The mixture was transferred to a glass fiber matrix which is in liquid communication with an absorbent pad (such as a disposable IMx® cartridge available from Abbott Laboratories, Ill.) and the fluorescence was measured with a fluorometer that uses a mercury arc lamp as its light source (as described by Fiore, M. et al 1988. Clin. Chem 34/9:1726–1732, the contents of which are incorporated herein by reference). The extent of fluorescence quenching is due to total hemoglobin. The matrix was washed three times with 200 ILL of the ammonium acetate buffer containing 0.20 mM methyl-umbelliferone. The fluorescence was again

TABLE 2

| Sample | Fluorescence (cts/sec) Total Hb/Gly Hb | [Total Hb] (mM) | [Gly Hb] (mM) | % Gly Hb |
|---|---|---|---|---|
| 0.0 mM* | 12279/— | — | — | — |
| 0.1 mM* | 8391/— | — | — | — |
| 0.6 mM* | 5670/— | — | — | — |
| 2.9 mM* | 1665/— | — | — | — |
| Normal Control | 3437/8305 | 1.58 | 0.11 | 7.0 |
| Middle Control | 3599/7656 | 1.48 | 0.18 | 12.2 |
| High Control | 3049/6492 | 1.82 | 0.38 | 20.9 |

*Hemoglobin Calibrator from Pierce Chemical Company, IL.

measured. The extent of fluorescence quenching is due to the glycated hemoglobin. The concentration of total hemoglobin ([Total Hb]) and glycated hemoglobin ([Gly Hb]) can be obtained from a standard curve generated from 0, 0.1, 0.6, 2.9 mM Hemoglobin Calibrators (see Table 2). The percent glycated hemoglobin (% Gly Hb), which is the ratio of glycated hemoglobin to total hemoglobin, can also be determined (see Table 2).

EXAMPLE 2

Fifty microliters (50 μL) of each sample of known hemoglobin concentration shown in Table 3 were mixed with 200 μL of 0.25 mM methylumbelliferone in 50 mM ammonium acetate buffer at pH 8.0 containing 50 mM $MgCl_2$ and the mixture was transferred onto the fiber matrix in liquid communication with an absorbent pad (such as a disposable IMx® cartridge available from Abbott Laboratories, Ill.). The fluorescence was immediately measured with a fluorometer that uses a mercury arc lamp as its light source (as described by Fiore, M. et al 1988. Clin. Chem 34/9:1726–1732, the contents of which are incorporated herein by reference). The results, shown in Table 3, illustrate that the fluorescence intensity (in millivolts) decreases with increasing hemoglobin concentration.

TABLE 3

| [Hb] (mM) | Fluorescence (mV) |
|---|---|
| 0.000 | 4.95 |
| 0.005 | 4.50 |
| 0.010 | 4.28 |
| 0.015 | 3.97 |
| 0.030 | 3.30 |
| 0.070 | 2.65 |
| 0.140 | 1.72 |
| 0.350 | 0.70 |
| 0.800 | 0.40 |

EXAMPLE 3

The fluorescence quenching due to Total Hemoglobin of the samples shown in Table 4 was determined by mixing 50 μL Of each sample with 200 μL of 0.25 mM methylumbelliferone in 50 mM ammonium acetate buffer at pH 8.0 containing 50 mM $MgCl_2$, transferring the mixture onto the fiber matrix which is in liquid communication with an absorbent pad (such as a disposable IMx® cartridge available from Abbott Laboratories, Ill., and measuring the fluorescence with a fluorometer that uses a mercury arc lamp as its light source (as described by Fiore, M. et al 1988. Clin. Chem 34/9:1726–1732, the contents of which are incorporated herein by reference).

The fluorescence quenching due to the Glycated Hemoglobin of the samples shown in Table 4 was determined by mixing 50 μL of each sample with 200 μL of 0.25 mM methylumbelliferone in 50 mM ammonium acetate buffer at pH 8.0 containing 50 mM $MgCl_2$ and 50% (v/v) dihydroxyboryl resin (Glyco-gel), transferring the mixture onto the fiber matrix of an IMx® disposable cartridge, washing the matrix with with 300 Ill. of the ammonium acetate buffer containing 0.20 mM methylumbelliferone, and measuring the fluorescence on the fiber matrix using an IMx® instrument. The fluorescence quenching was then measured again after the matrix was washed with the ammonium acetate buffer containing 0.20 mM methylumbelliferone and 200 mM sorbitol. All the fluorescence readings are in millivolts.

TABLE 4

| Sample | Fluorescence (mV) | | |
|---|---|---|---|
| | Total Hb | Gly Hb[1] | Gly Hb[2,3] |
| 5% Gly Hb | 0.94 | 2.47 | 3.97 |
| 17% Gly Hb | 0.92 | 1.79 | 3.95 |

[1]First glycated hemoglobin measurement.

TABLE 4-continued

| | Fluorescence (mV) | | |
|---|---|---|---|
| Sample | Total Hb | Gly Hb[1] | Gly Hb[2,3] |

[2]Glycated hemoglobin measurement after sorbitol wash.
[3]Fluorescence in the absence of hemoglobin is 4.06 mV.

The sorbitol clearly displaced substantially all of the glycated hemoglobin present on the matrix.

EXAMPLE 4

Hemoglobin and glycated hemoglobin calibrators were prepared by serial dilution of red cell lysed human blood samples that have been artificially glycated to about 40% glycated hemoglobin (by Glyc-Affn, Isolab) by mixing 250 mM glucose at 37° C. for 96 hours (as described in U.S. patent application Ser. No. 717,558, entitled "Rapid Determination Of Glycated Hemoglobin", which enjoys common ownership and is herein incorporated by reference). The Glyc-Affn Assay (Isolab, Inc., Ohio) was used to measure the concentration of hemoglobin and glycated hemoglobin in a sample. The calibrator with the highest concentration of glycated hemoglobin (F cal) was prepared by admixing low and high bulk glycated human hemoglobin samples (prepared according to the method disclosed in U.S. patent application Ser. No. 717,558, entitled "Rapid Determination Of Glycated Hemoglobin", which enjoys common ownership and is herein incorporated by reference) until a 20% glycated hemoglobin concentration was achieved and then diluting the mixture with phosphate buffered saline until a total hemoglobin concentration of 12 mM (19.3 g/dL) was achieved. Other calibrators were then prepared from the F cal by dilution with phosphate buffered saline to a final total hemoglobin concentration of 9, 6, 3, and 1 mM (E, D, C and B calibrators, respectively). A sixth calibrator was prepared from phosphate buffered saline and had a total hemoglobin concentration of 0 mM. The calibrator hemoglobin and glycated hemoglobin concentrations are listed in Table 1. Typical calibration curves for total hemoglobin and glycated hemoglobin are shown in FIG. 1 and were prepared according to Example 6.

EXAMPLE 5

Boronate polyacrylic acid was prepared as follows. Polyacrylic acid (48.6 g) in 25 mM MES Buffer (pH 5.5) and meta-aminobenzeneboronic acid (8 g) in 25 mM MES Buffer (pH 5.5) were mixed and the pH was adjusted to 6.1. 1-Ethyl-3-(3-dimethylaminopropyl)carbodiimide (EDAC) (20.7 g) was added. The mixture was stirred at room temperature for 50 minutes and the reaction was quenched by the addition of 24% glycine at pH 9.8. The reaction was diafiltered against six volumes of 50 mM Taurine (pH 9.0) and sterile filtered.

EXAMPLE 6

The assay format herein was performed on an IMx® instrument (commercially available from Abbott Laboratories, IL and described in EP-A-288 793 and in Fiore et al, Clin. Chem. 34/9; 1726–1732 (1988) both of which are incorporated herein by reference). The red blood cells in a sample (10 µL) were lysed by adding lysing solution (70 µL of 1% w/v Triton X-100 and 0.70 mM 4-methyl-umbelliferone in 50 mM HEPES buffer (pH 8.0) containing 50 mM MgCl$_2$, 100 mM sodium chloride and 0.1% sodium azide) and polyanion reagent solution (0.9% w/v of the boronate polyacrylic acid from Example 5 in 50 mM Taurine at pH 9.0) followed by two cycles of rapidly aspirating and dispensing the mixture into and out of the instrument pipettor. This process gave almost instantaneous hemolysis of fresh whole blood.

A second mixture is prepared from this first mixture by transferring an aliquot (17 µL) of this first mixture to the reaction well of the IMx® disposable cartridge and adding 170 µL of 100 mM Tris buffer at pH 7.5 containing 300 mM sodium chloride and 40µL of sorbitol wash (10% w/v sorbitol and 17.5 mM 4-methyl-umbelliferone in 100 mM Tris buffer at pH 7.5 containing 300 mM sodium chloride) to the reaction well.

A second aliquot (50 µL) of the first mixture is transferred to the fiber matrix of the IMx® disposable cartridge (available from Abbott Laboratories, Ill.) which is coated with a 0.2% w/v (5.425 g/L) Merquat® 100 (commercially available from Calgon Corporation) solution (6.06 g/L Tris buffer at pH 7.5 containing 6.35 g/L Tromethane, 5.84 g/L sodium chloride, 1 g/L sucrose, and 0.95 mL/L fish gelatin). The boronate polyacrylic acid glycated hemoglobin complexes bind to the Merquat® 100 and the matrix is washed with 240 'L of wash solution (7.5 mM 4-methyl-umbelliferone in 50 mM Taurine buffer (pH 9.0) 0 containing 25 mM asparagine, 25 mM methionine, 100 mM MgCl$_2$, and 0.1% sodium azide) to remove substantially all of the non-glycated hemoglobin. The fluorescence quenching due to the glycated hemoglobin present on the matrix is then measured.

The matrix is washed with about 50 µL of sorbitol wash. Sorbitol competes with glycated hemoglobin for the bound affinity reagent and the glycated hemoglobin is removed. An aliquot (50 µL) of the second mixture is transferred to the matrix, and the fluorescence quenching due to both glycated and non-glycated hemoglobin is measured. The total and glycated hemoglobin concentrations are determined from separate calibration curves prepared with the calibrators of Example 4 following this assay format, and the % glycated hemoglobin is calculated.

EXAMPLE 7

Figure 2:
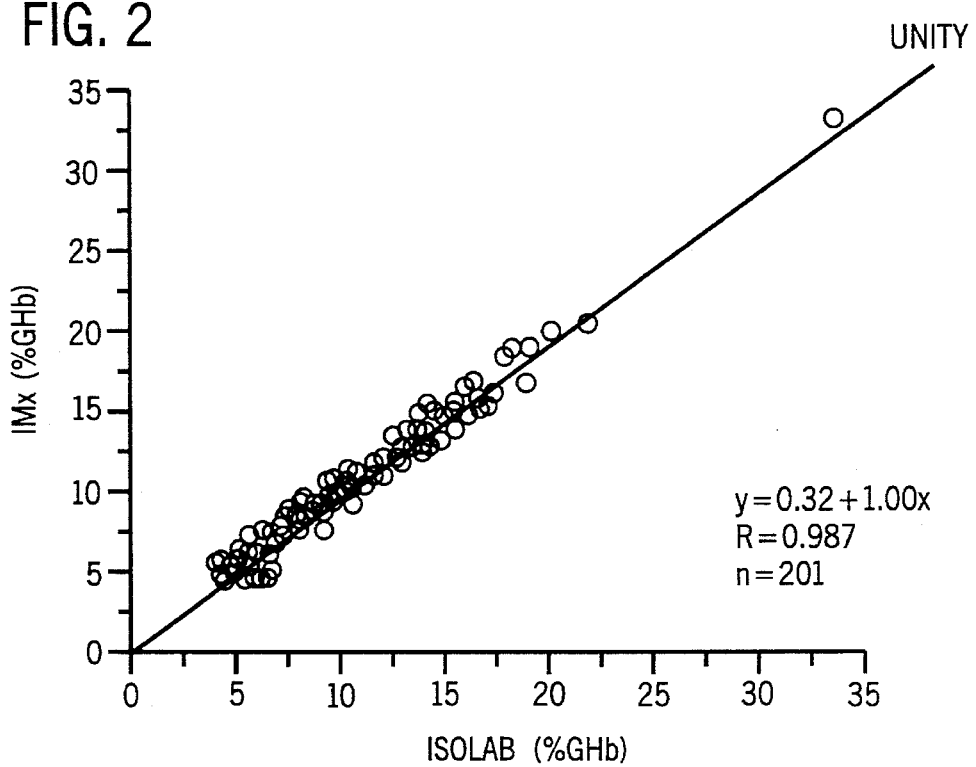
FIG. 2: A correlation curve of 201 patient samples tested for % glycated hemoglobin using this invention (Example 6) and Glyc-Affn assay of Isolab.

Using the assay format of Example 6, 201 patient samples were tested and compared to the results obtained from the Glyc-Affn assay of Isolab. The data is shown in the correlation curve of FIG. 2.

EXAMPLE 8

Figure 3:
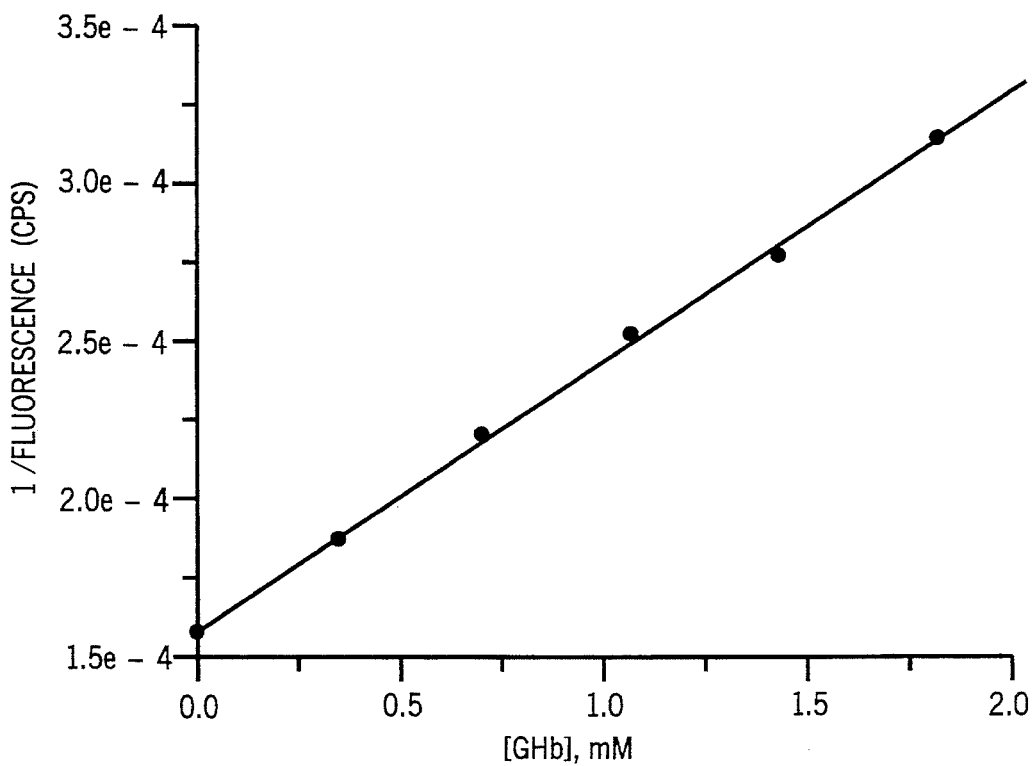
FIG. 3: A typical calibration curve (Reciprocal of Fluorescence in counts per second versus hemoglobin concentration in mM) for glycated hemoglobin using the calibrators of Example 4 in the assay format of Example 8 of the present invention.
Figure 4:
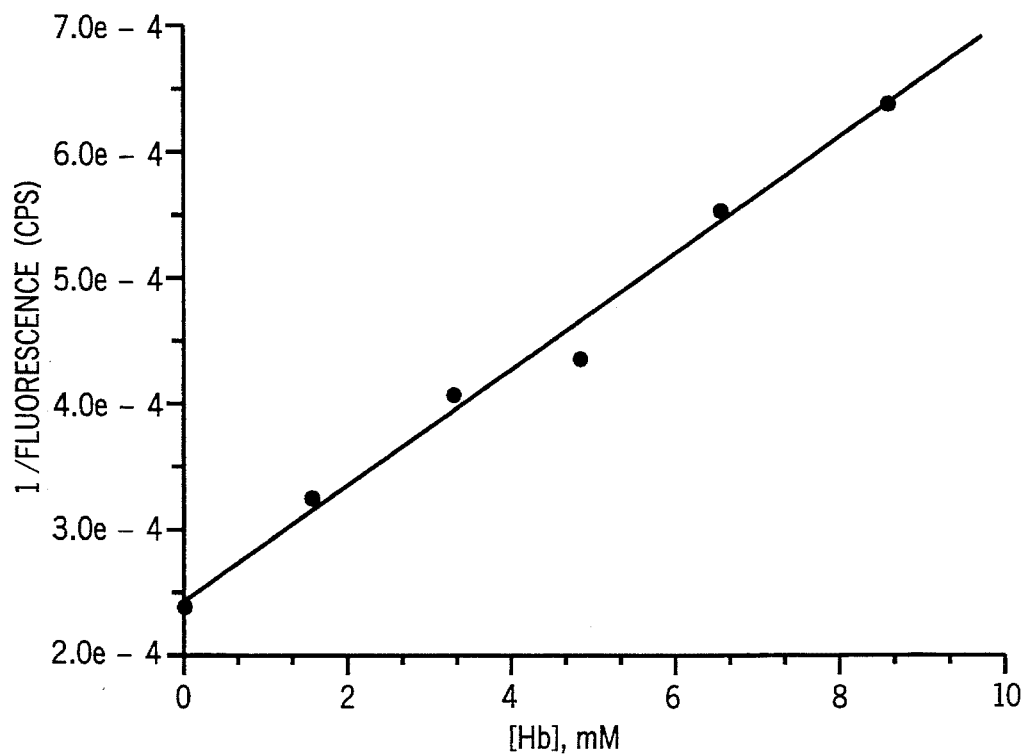
FIG. 4: A typical calibration curve (Reciprocal of Fluorescence in counts per second versus hemoglobin concentration in mM) for total hemoglobin using the calibrators of Example 4 in the assay format of Example 8 of the present invention.
Figure 5:
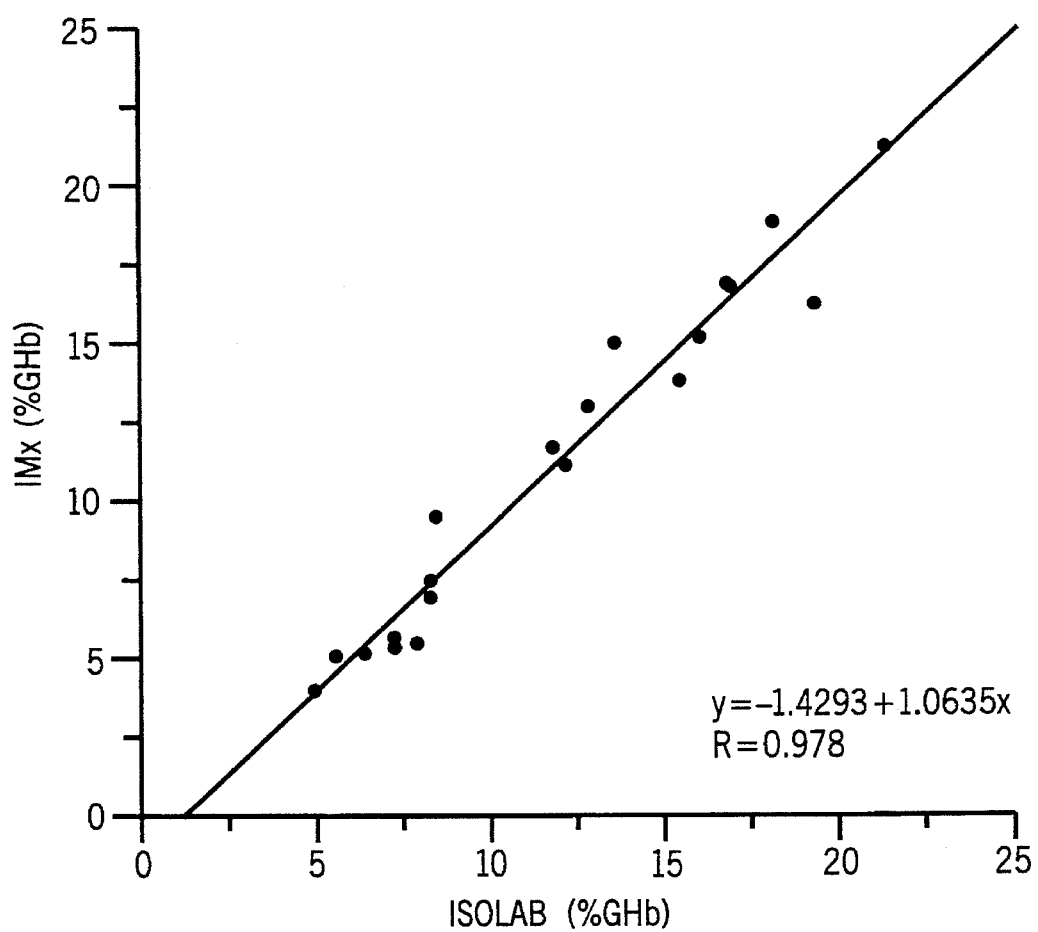
FIG. 5: A correlation curve of 20 patient samples tested for % glycated hemoglobin using this invention (Example 8) and Glyc-Affn assay of Isolab.

Glycated hemoglobin was measured using boronate acrylamide microparticles (prepared using the methods of Hageman, et al., Anal. Biochem. 80:547 (1977), and Inman, et al., Biochem. 8:4078 (1969)) and a modification of the assay format of Example 6, modified in that the glycated hemoglobin was measured after the total hemoglobin measurement. A 1% (w/v) solution of the borate microparticles were used instead of the boronate polyacrylic acid. Calibration curves were prepared from the calibrators of Example 4 and are shown in FIGS. 3 and 4. Twenty patient samples were tested using this assay format and the results were compared to the results obtained from the Glyc-Affn assay of Isolab. FIG. 5 shows the correlation curve of the 20 patient samples tested for % glycated hemoglobin using this assay format and Glyc-Affn assay of Isolab.

The embodiments described and the alternative embodiments presented are intended as examples rather than as limitations. Thus, the description of the invention is not intended to limit the invention to the particular embodiments disclosed, but it is intended to encompass all equivalents and subject matter within the spirit and scope of the invention as described above and as set forth in the following claims.

What is claimed is:

1. A method of determining a preselected hemoglobin in a blood sample wherein said preselected hemoglobin is selected from the group consisting of total hemoglobin, non-glycated hemoglobin and glycated hemoglobin, said method comprising the steps of:

a. exposing said blood sample to a lysing agent to lyse red bloods in said sample to release said total hemoglobin;
   b. contacting said lysed blood sample with a fluorescent dye;
   c. determining fluorescence quenching of said fluorescent dye caused by said preselected hemoglobin with the proviso that when said preselected hemoglobin is said non-glycated hemoglobin or said glycated hemoglobin, said lysed blood sample is first separated into a non-glycated hemoglobin fraction and a glycated hemoglobin fraction prior to determining said fluorescence quenching of said non-glycated or said glycated hemoglobin in its respective fraction; and
   d. determining the concentration of said preselected hemoglobin in said blood sample by comparing said fluorescence quenching of step c. to a calibration curve obtained from determining fluorescence quenching of said fluorescent dye by known concentrations of said preselected hemoglobin.

2. The method of claim 1 wherein said lysing step comprises contacting said blood sample with a detergent.

3. The method of claim 1 wherein said step of separating said glycated hemoglobin comprises contacting said lysed blood sample with a specific binding member specific for said glycated hemoglobin to form a specific binding member/glycated hemoglobin complex and separating said complex from said lysed blood sample to obtain said glycated hemoglobin fraction.

4. The method of claim 3 wherein said specific binding member is physically or chemically bound to a solid phase.

5. The method of claim 4 wherein said solid phase is a particle, a film, a fiber, a tube, or a well.

6. The method of claim 3 wherein said specific binding member is covalently bound to a first polyionic compound that binds to a second polyionic compound of opposite charge which is bound to a solid phase.

7. The method of claim 6 wherein said first polyionic compound is selected from the group consisting of polyaspartic acid, heparin, carboxymethyl amylose, polyglutamic acid and polyacrylic acid.

8. The method of claim 6 wherein said second polyionic compound is a polymeric quaternary ammonium compound or diethylaminoethyl-dextran.

9. The method of claim 8 wherein said polymeric quaternary ammonium compound is MERQUAT 100, a cationic homopolymer of dimethyldiallylammonium chloride.

10. The method of claim 6 wherein said solid phase is a fiber matrix.

11. The method of claim 6 wherein said specific binding member is selected from the group consisting of an affinity reagent comprising a dihydroxyboronate moiety in a tetrahedral anionic form, an anti-glycated hemoglobin antibody, and a lectin which specifically binds glycated hemoglobin.

12. The method of claim 4 wherein said fluorescent dye is fluorescein, rhodamine, umbelliferone, or derivatives thereof.

13. A method of determining the ratio of glycated hemoglobin to total hemoglobin in a blood sample comprising the steps of:

a. exposing said blood sample to a lysing agent to lyse red blood cells in said blood sample to release said total hemoglobin;
   b. contacting said lysed blood sample with a fluorescent dye;
   c. providing a first and a second aliquot of said lysed blood sample;
   d. determining the concentration of said total hemoglobin by measuring fluorescence quenching of said fluorescent dye in said first aliquot caused by said total hemoglobin;
   e. separating said glycated hemoglobin from said total hemoglobin in said second aliquot to obtain a glycated hemoglobin fraction and a non-glycated hemoglobin fraction;
   f. determining the concentration of said glycated hemoglobin
      (1) directly by measuring fluorescence quenching of said fluorescent dye in said glycated hemoglobin fraction caused by said glycated hemoglobin or
      (2) indirectly by measuring fluorescence quenching of said fluorescent dye in said non-glycated fraction caused by said non-glycated hemoglobin to determine the concentration of said non-glycated hemoglobin which is then subtracted from the total hemoglobin concentration to obtain the concentration of said glycated hemoglobin; and
   g. dividing said glycated hemoglobin concentration by said total hemoglobin concentration to obtain the ratio of glycated hemoglobin to total hemoglobin in said blood sample.

14. The method of claim 13 wherein said step of separating said glycated hemoglobin comprises contacting said second aliquot of said lysed blood sample with a specific binding member specific for glycated hemoglobin to form a specific binding member/glycated hemoglobin complex and separating said complex from said second aliquot of said lysed blood sample to obtain said glycated hemoglobin fraction.

15. The method of claim 14 wherein said specific binding member is covalently bound (i) to a particle which is bound to a fiber matrix or (ii) to a first polyionic compound which is bound to a fiber matrix of opposite charge.

16. A method for determining the ratio of glycated hemoglobin to total hemoglobin in a blood sample comprising the steps of:

a. exposing said blood sample to a lysing agent to lyse red blood cells in said blood sample to release said total hemoglobin;
   b. contacting said lysed blood sample with a fluorescent dye;
   c. providing a first and a second aliquot of said lysed blood sample;
   d. contacting said first aliquot with a polyanion affinity reagent comprising tetrahedral dihydroxyboronate moieties which specifically react with cis-diol moieties on said glycated hemoglobin to form an anionic affinity complex;
   e. contacting said first aliquot of step d. with a cationic fiber matrix to immobilize said anionic affinity complex thereon;
   f. washing said cationic fiber matrix of step e. to remove unbound components of said first aliquot;
   g. determining the concentration of said glycated hemoglobin by measuring fluorescence quenching of said fluorescent dye caused by said glycated hemoglobin immobilized on said washed cationic fiber matrix of step f.;

h. eluting said glycated hemoglobin from said washed cationic fiber matrix of step f.;

i. contacting said second aliquot with the cationic fiber matrix of step h.;

j. determining the concentration of said total hemoglobin by measuring fluorescence quenching of said fluorescent dye in said first aliquot caused by said total hemoglobin; and k. dividing said glycated hemoglobin concentration by said total hemoglobin concentration to obtain the ratio of glycated hemoglobin to total hemoglobin in said blood sample.

17. The method of claim 16 wherein said eluant is a 1,2 cis-diol compound.

18. The method of claim 17 wherein said 1,2 cis-diol compound is sorbitol.

19. A method of determining the ratio of glycated hemoglobin to total hemoglobin in a blood sample comprising:

a. exposing said blood sample to a lysing agent to lyse red blood cells in said blood sample to release said total hemoglobin;

b. contacting said lysed blood sample with a fluorescent dye;

c. determining the concentration of said total hemoglobin by measuring fluorescence quenching of said fluorescent dye caused by said total hemoglobin in aliquot of said lysed blood sample;

d. fractionating said aliquot into a glycated hemoglobin fraction and a non-glycated hemoglobin fraction;

e. determining the concentration of said glycated hemoglobin
  (1) directly by measuring fluorescence quenching of said fluorescent dye in said glycated hemoglobin fraction caused by said glycated hemoglobin or
  (2) indirectly by measuring fluorescence quenching of said fluorescent dye in said non-glycated fraction caused by said non-glycated hemoglobin fraction to determine the concentration of said non-glycated hemoglobin which is then subtracted from the total hemoglobin concentration to obtain the concentration of said glycated hemoglobin; and f. dividing said glycated hemoglobin concentration by said total hemoglobin concentration to obtain the ratio of glycated hemoglobin to total hemoglobin in said blood sample.

20. A method of determining the ratio of glycated hemoglobin to total hemoglobin in a blood sample comprising the steps of:

a. exposing said blood sample to a lysing agent to lyse red blood cells in said blood sample to release said total hemoglobin;

b. fractioning said lysed blood sample into a glycated hemoglobin fraction and a non-glycated hemoglobin fraction;

c. contacting said glycated hemoglobin fraction and said non-glycated hemoglobin fraction with a fluorescent dye;

d. determining the concentrations of said glycated hemoglobin and said non-glycated hemoglobin by measuring fluorescent quenching caused by said glycated hemoglobin and said non-glycated hemoglobin in their respective fractions;

e. adding said glycated hemoglobin concentration to said non-glycated hemoglobin concentration to obtain the concentration of said total hemoglobin; and, f. dividing said glycated hemoglobin concentration by said total hemoglobin concentration to obtain the ratio of glycated hemoglobin to total hemoglobin in said blood sample.

21. A method for determining the ratio of glycated hemoglobin to total hemoglobin in a blood sample comprising the steps of:

a. exposing said blood sample to a lysing agent to lyse red blood cells in said blood sample to release said total hemoglobin;

b. contacting said lysed blood sample with a fluorescent dye;

c. providing a first and a second aliquot of said lysed blood sample, d. capturing said glycated hemoglobin in said first aliquot on a fiber matrix comprising a specific binding member which specifically binds said glycated hemoglobin;

e. determining the concentration of said glycated hemoglobin by measuring fluorescence quenching of said fluorescent dye caused by said glycated hemoglobin captured on said fiber matrix;

f. eluting said captured glycated hemoglobin from said fiber matrix with an eluant;

g. applying said second aliquot to said fiber matrix of step f.;

h. and determining the concentration of said total hemoglobin by measuring fluorescence quenching of said fluorescent caused by said applied total hemoglobin; and i. dividing said glycated hemoglobin concentration by said total hemoglobin concentration to obtain the ratio of glycated hemoglobin to total hemoglobin in said blood sample.

22. The method of claim 16 wherein said specific binding member is a polyanion affinity reagent comprising tetrahedral dihydroxyboronate moieties which specifically react with cis-diol moieties on said glycated hemoglobin and said eluant is a 1,2 cis-diol compound.

* * * * *

UNITED STATES PATENT AND TRADEMARK OFFICE
CERTIFICATE OF CORRECTION

PATENT NO. : 5,478,754
DATED : December 26, 1995
INVENTOR(S) : Douglas R. Brandt, et al.

It is certified that error appears in the above-indentified patent and that said Letters Patent is hereby corrected as shown below:

On the title page , item [73]

In the abstract, last line, change "phase" to

--solid phase--.

Column 5, line 17, change "Iectin" to

--lectin--.

Column 10, line 51, change "lll" to

--µL--.

Column 12, line 23, change " 'L" to

--µL--.

UNITED STATES PATENT AND TRADEMARK OFFICE
CERTIFICATE OF CORRECTION

PATENT NO. : 5,478,754
DATED : December 26, 1995
INVENTOR(S) : Douglas R. Brandt et al.

It is certified that error appears in the above-indentified patent and that said Letters Patent is hereby corrected as shown below:

Column 12, line 24, delete

-- 0 --.

Column 13, line 59, change "4" to

-- 1 --.

Signed and Sealed this

Nineteenth Day of November, 1996

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,478,754
DATED : December 26, 1995
INVENTOR(S) : D.R. Brandt, et al.

It is certified that error appears in the above-indentified patent and that said Letters Patent is hereby corrected as shown below:

On the title page, item [75], insert --David H. Wilson, Evanston,-- before "all of Ill."

Signed and Sealed this

Tenth Day of December, 1996

Attest:

BRUCE LEHMAN

Attesting Officer     Commissioner of Patents and Trademarks